(12) United States Patent
Peterson et al.

(10) Patent No.: US 10,117,609 B2
(45) Date of Patent: *Nov. 6, 2018

(54) METHOD FOR DISTRIBUTING CONTACT INFORMATION BETWEEN APPLICATIONS

(71) Applicant: Neustar, Inc., Sterling, VA (US)

(72) Inventors: Jon Peterson, Sterling, VA (US); Webb Dryfoos, Sterling, VA (US); Peter Charlier Davis, Sterling, VA (US)

(73) Assignee: Neustar, Inc., Sterling, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/487,178

(22) Filed: Apr. 13, 2017

(65) Prior Publication Data

US 2017/0281061 A1    Oct. 5, 2017

Related U.S. Application Data

(63) Continuation of application No. 12/705,268, filed on Feb. 12, 2010, now Pat. No. 9,636,053.

(51) Int. Cl.
*G06F 15/16* (2006.01)
*G06F 13/00* (2006.01)
*A61B 5/145* (2006.01)
*G01N 33/543* (2006.01)
*A61B 5/1486* (2006.01)

(52) U.S. Cl.
CPC ........ *A61B 5/14546* (2013.01); *A61B 5/1486* (2013.01); *G01N 33/5438* (2013.01); *G01N 33/54393* (2013.01); *A61B 5/14532* (2013.01)

(58) Field of Classification Search
CPC ... H04L 61/1594; H04L 63/04; H04L 67/104; H04L 67/306
USPC ................................ 370/242, 400; 711/163
See application file for complete search history.

(56) References Cited

U.S. PATENT DOCUMENTS

| | | | | |
|---|---|---|---|---|
| 2002/0049828 A1* | 4/2002 | Pekarek-Kostka | ..... | H04L 29/06 709/217 |
| 2002/0152265 A1* | 10/2002 | Felman | ................... | H04L 29/06 709/203 |
| 2003/0177246 A1* | 9/2003 | Goodman | ............. | H04L 67/104 709/228 |
| 2003/0186704 A1* | 10/2003 | Tamura | ............. | H04L 29/06027 455/450 |
| 2005/0266835 A1* | 12/2005 | Agrawal | ................ | G06Q 10/10 455/414.3 |
| 2007/0038720 A1* | 2/2007 | Reding | ................ | G06Q 10/107 709/217 |
| 2009/0089292 A1* | 4/2009 | Cheah | .................... | G06Q 10/06 |

(Continued)

*Primary Examiner* — Charles C Jiang
*Assistant Examiner* — Ryan Kavleski
(74) *Attorney, Agent, or Firm* — Mahamedi IP Law LLP (57) ABSTRACT

A method and system for distributing contacting information between applications is provided. The system preferably uses an ENUM-type protocol and a middleware tool kit to associate telephone numbers to other identifying information, such as e-mail addresses or URLs for web sites. The system enables the associated contacting information to be shared across multiple applications that may be implemented on a computer or a mobile telephony device. Information is shared only after verification that a requester is authorized to receive the requested contacting information.

20 Claims, 4 Drawing Sheets

(56) References Cited

U.S. PATENT DOCUMENTS

2010/0082761 A1* 4/2010 Nguyenphu ...... G06F 17/30165
           709/206
2012/0016939 A1* 1/2012 Cheah .................... G06Q 10/06
           709/205

* cited by examiner

METHOD FOR DISTRIBUTING CONTACT INFORMATION BETWEEN APPLICATIONS

RELATED APPLICATIONS

This application is a Continuation of U.S. patent application Ser. No. 12/705,268, filed Feb. 12, 2010, which is hereby incorporated by reference in its entirety for all purposes.

BACKGROUND OF THE INVENTION

Field of the Invention

The present invention relates to the field of electronic communications. More particularly, the invention relates to sharing contact information across applications such as mobile telephones and the Internet.

Many existing technologies use ENUM or ENUM-like mechanisms for resolving telephone numbers into the URIs that identify network services. Many systems also enable portability of contact books, i.e., allowing a user to transfer a list of contacts from one computer to another, or synchronizing between mobile and desktop systems, or allowing a user to purchase a new mobile device and then to download or otherwise transfer a contact book from the old device. There are also conventional systems that use reciprocal authorization. For example, some instant messaging systems enable two parties to identify themselves as "buddies", who are then able to detect each other's presence, or online status, and to send messages to one another.

However, these conventional systems primarily address situations in which contact information is being transferred between devices controlled by a single user. In the instant messaging example, although two users are involved, reciprocal authorization is required, and the functionality is relatively limited. Accordingly, there is a need for a capability to share contact information between multiple users across applications simply and efficiently.

SUMMARY OF THE INVENTION

In one aspect, the invention provides a method for sharing contact information of a first user between a first application and a second application. The method comprises using a server on a computer network to perform the steps of: identifying first information relating to the first user; provisioning identification data associated with the first information; storing the provisioned data and the first information together in a first database; receiving a request for the provisioned data from a second user; determining whether the second user is authorized to obtain the provisioned data; when a determination is made that the second user is authorized to obtain the provisioned data, retrieving the provisioned data from the first database; and transmitting the provisioned data to a device associated with the second user.

The method may further comprise the step of receiving from the first user data for identifying authorized potential users. The step of determining whether the second user is authorized to obtain the provisioned data may further comprise determining whether the data for identifying authorized potential users includes data for identifying the second user. The step of identifying first information relating to the first user may further comprise receiving a prompt and the first information from a device associated with the first user. The first information may comprise a telephone number. The device associated with the first user may comprise a mobile telephony device associated with the first user. The first information may comprise a telephone number associated with the device associated with the first user.

The mobile telephony device associated with the first user may comprise a middleware tool kit. The middleware tool kit may comprises a first network interface configured to transmit prompts and information over the computer network; a second network interface configured to transmit queries over the computer network and to receive responses to the transmitted queries; a first application programming interface (API) for receiving provisioning requests from applications; and a second API for receiving information requests from applications and for transmitting responses to the information requests to the requesting applications.

The provisioned data may comprise at least one Uniform Resource Indicator (URI). The at least one provisioned URI may be associated with an identifier selected from the group consisting of a telephone number, an e-mail address, an instant messaging handle, and a Uniform Resource Locator (URL) of a web page. The device associated with the second user may comprise a mobile telephony device associated with the second user. The step of transmitting the provisioned data may further comprise transmitting an SMS text message to the mobile telephony device associated with the second user. The step of provisioning identification data associated with the first information may further comprise transmitting an SMS text message to a device associated with the first user to determine whether the identification data to be provisioned is correctly associated with the first information.

In another aspect, the invention provides a system for sharing contact information of a first user between a first application and a second application. The system comprises a server configured for communicating with client devices over a computer network. The server is configured to perform the steps of: identifying first information relating to a first user; provisioning identification data associated with the first information; storing the provisioned data and the first information together in a first database; receiving a request for the provisioned data from a second user; determining whether the second user is authorized to obtain the provisioned data; when a determination is made that the second user is authorized to obtain the provisioned data, retrieving the provisioned data from the first database; and transmitting the provisioned data to a client device associated with the second user.

The server may be further configured to perform the steps of receiving from the first user data for identifying authorized potential users, and determining whether the data for identifying authorized potential users includes data for identifying the second user. The server may be further configured to perform the step of receiving a prompt and the first information from a client device associated with the first user. The first information may comprise a telephone number. The client device associated with the first user may comprise a mobile telephony device associated with the first user. The first information may comprise a telephone number associated with the client device associated with the first user.

The mobile telephony device associated with the first user may comprise a middleware tool kit. The middleware tool kit may comprise a first network interface configured to transmit prompts and information over the computer network; a second network interface configured to transmit queries over the computer network and to receive responses to the transmitted queries; a first application programming interface (API) for receiving provisioning requests from applications; and a second API for receiving information requests from applications and for transmitting responses to the information requests to the requesting applications.

The provisioned data may comprise at least one Uniform Resource Indicator (URI). The at least one provisioned URI may be associated with an identifier selected from the group consisting of a telephone number, an e-mail address, an instant messaging handle, and a Uniform Resource Locator (URL) of a web page. The client device associated with the second user may comprise a mobile telephony device associated with the second user. The server may be further configured to perform the step of transmitting an SMS text message to the mobile telephony device associated with the second user. The server may be further configured to perform the step of transmitting an SMS text message to a device associated with the first user to determine whether the identification data to be provisioned is correctly associated with the first information.

DETAILED DESCRIPTION OF THE INVENTION

The present inventors have recognized the need to enable sharing of contact information across multiple applications and among multiple users in a reasonably simple and efficient manner. Accordingly, it is an object of the present invention to provision ENUM in an automated and transparent way, while preventing public disclosure of contact information.

In a preferred embodiment of the invention, a system is designed to enable sharing of supplemental contact information between users of mobile telephones. When two mobile phone users know one another's telephone numbers, the system allows them to learn other ways of communicating over the Internet, for example email addresses or addresses for instant messaging. Applications can leverage this knowledge to help users discover contacts who also utilize the same application.

The invention was inspired by ENUM, in particular by the difficulty of seeding directories for translating telephone numbers into Internet identifiers. Many mobile telephones, notably the iPhone, have rich contact books with numerous identifiers that could be published via ENUM. The difficulties are that provisioning ENUM is typically a cumbersome step, and many users are reluctant to make their contact information public. Accordingly, in a preferred embodiment of the invention, the provisioning is made transparent, and reciprocal authorization whitelisting is used as a baseline, thereby preventing public disclosure of contact information.

Figure 1:
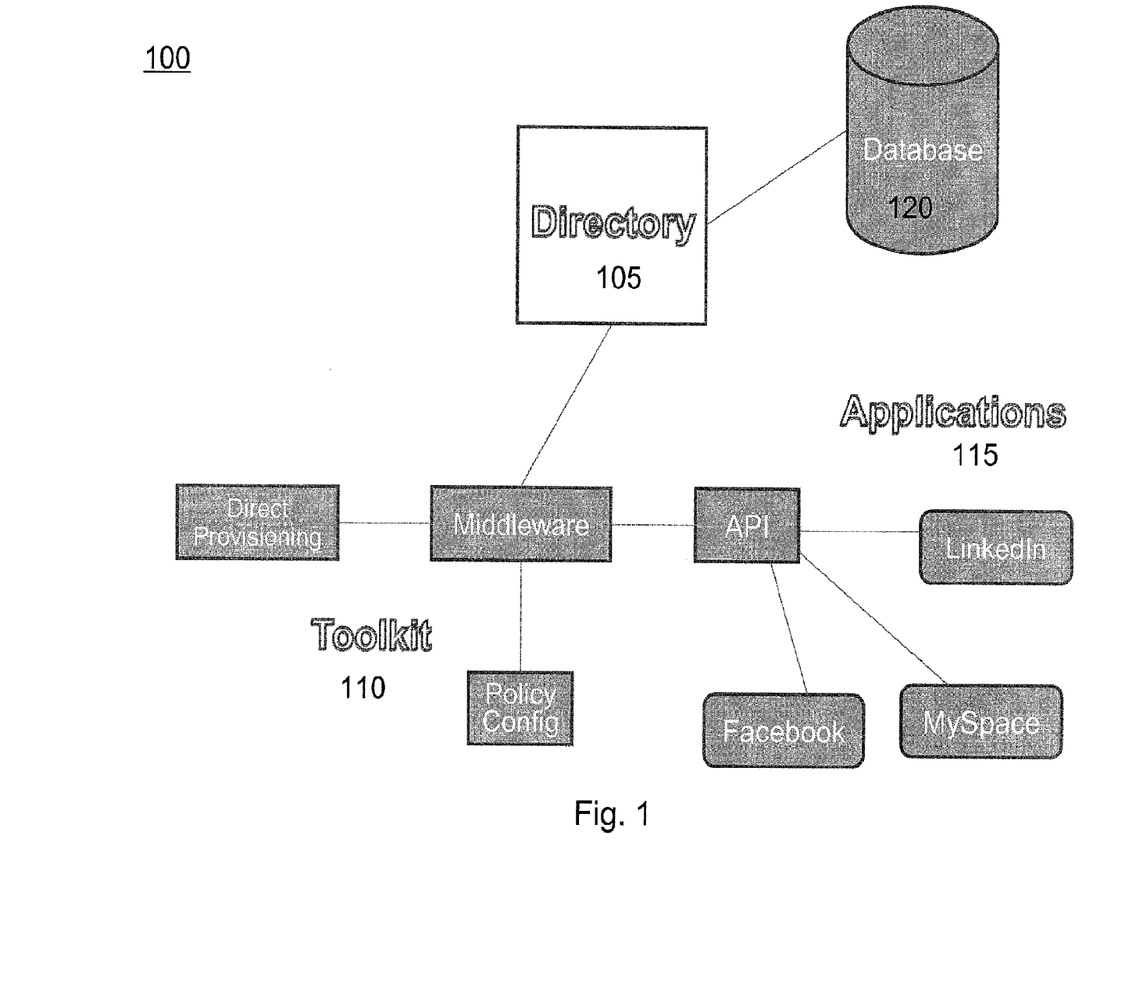
FIG. 1 illustrates a block diagram of an architecture for a system for sharing contacting information across applications according to a preferred embodiment of the invention.

Referring to FIG. 1, a block diagram of an architecture of a system 100 according to a preferred embodiment of the invention is shown. The system 100 includes a directory 105 and a middleware toolkit 110 which are leveraged by applications 115 to discover new identifiers associated with the telephone number of a contact. The system 100 also includes an authorization database 120 which can be accessed by the directory 105 in order to verify that a requesting client is authorized to receive contacting information in response to a request for same. In a broad sense, the system 100 is designed to translate one identifier into a set of different identifiers. The identifier so translated is, for the sake of readability, hereafter exemplified by a telephone number, and although the telephone number is used for the translated identifier in the preferred implementation, the invention is not limited to the use of telephone numbers for translated identifiers.

Figure 2:
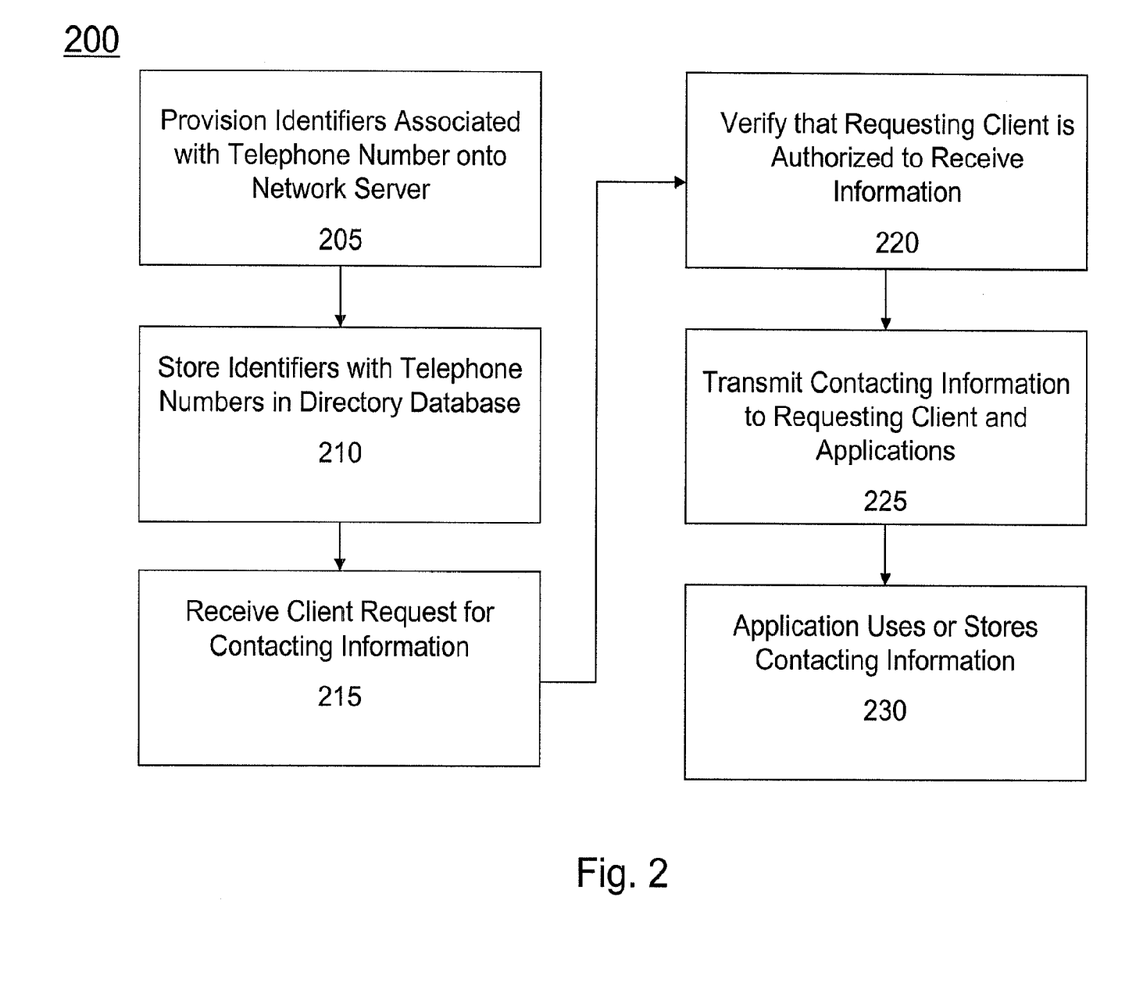
FIG. 2 shows a flow chart that illustrates a method for sharing contacting information across applications according to a preferred embodiment of the invention.

Referring to FIG. 2, a flow chart 200 that illustrates a method of sharing contacting information across applications according to preferred embodiment of the present invention is shown. In the first step 205, the identifiers associated with a telephone number are provisioned into a server on a computer network, either as a bulk operation or one by one, by various clients attached to the same computer network. In the second step 210, upon receiving the provisioning instructions from clients, the server stores that data in a database table, with the telephone number serving as the key and one or more identifiers associated with the telephone number serving as the value. In the third step 215, a translation is instigated by one such client, generally in order to acquire information provisioned by other clients, and performed by said server, which returns the response to the client.

In the fourth step 220, the server verifies that the requesting client is authorized to receive the requested information by consulting a second database, which includes information that identifies authorized senders of queries. The second database may be resident locally, or it may reside elsewhere on the network. Then, upon verification that the requesting client is so authorized, the server returns the identifiers in response to the client, and the client delivers the response to an application in step 225. Finally, in step 230, the application may make use of the identifiers immediately, or it may store them for future use or invocation by the user. If the identifiers are stored, they are stored for a specific lifetime, after which application must ask the client to make a new query to the server.

In the system 100, an application may learn identifiers of a user through manual input, as is the case with a contact book, or the application may actually assign identifiers to a use, as is the case with an instant messaging application in which a user registers a new identifier. The system 100 may be implemented, for example, where users commonly contact one another by dialing a telephone number, and where terminals commonly record the calling and called parties in a telephone conversation, thus building a list of contacts by telephone number. In this manner, the system 100 allows users to discover other communications and applications identifiers associated with their contacts, even if they know their contact only by telephone number.

Referring again to FIG. 1, the directory 105 is the back-end database that maintains the mappings from telephone numbers to various application identifiers, and also the server interface to that directory. The directory 105 is populated by the middleware toolkit 110, which sends provisioning information to the directory 105. The directory 105 is queried through the middleware toolkit 110 by applications 115 that want to acquire mappings for a particular telephone number. The directory 105 also maintains, or accesses externally, a list of contacts associated with a particular telephone number, in order to learn which telephone numbers are authorized to query for a particular application.

The middleware toolkit 110 is a software library that contains the necessary code to interface with the directory 105 over the Internet. Applications 115 use the middleware toolkit 110 to learn about the application identifiers associated with a particular telephone number. The application 115 is a communications application residing on a general purpose computer, be it a desktop or a mobile handset, that makes use of the middleware toolkit to learn and provision the application identifiers associated with a telephone number. The application 115 may be understood broadly to include any software used for personal communication on the Internet, including various messaging, real-time audio transmission, and gaming applications.

An identifier includes any information that represents a user within the scope of a particular communications system. Examples include telephone numbers, e-mail addresses, instant messaging handles, and the Uniform Resource Locator (URL) of a web page where a user might be reached. Calling, invoking, or dereferencing an application identifier typically causes the invocation of the application and contacts through the application the user has designated by the identifier.

The directory 105 resides on one or more servers. The server is preferably implemented by the use of one or more general purpose computers, such as, for example, a Sun Microsystems Fire F15k. Each of the middleware tool kit 110, the applications 115, and the authorization database 120 may also be implemented by the use of one or more general purpose computers, such as, for example, a typical personal computer manufactured by Dell, Gateway, or Hewlett-Packard; or more preferably, the middleware tool kit 110 and the applications 115 may be implemented on a smart mobile telephone, such as, for example, an Apple iPhone or a Blackberry Storm mobile telephone or a smart mobile telephone manufactured by Google. Each of the server and the client devices on which the middleware tool kit 110, the applications 115, and the authorization database 120 reside can include a microprocessor. The microprocessor can be any type of processor, such as, for example, any type of general purpose microprocessor or microcontroller, a digital signal processing (DSP) processor, an application-specific integrated circuit (ASIC), a programmable read-only memory (PROM), or the like. The server may use its microprocessor to read a computer-readable medium containing software that includes instructions for carrying out one or more of the functions of the directory 105, as further described below.

Each of the server and the client devices on which the middleware tool kit 110, the applications 115, and the authorization database 120 reside can also include computer memory, such as, for example, random-access memory (RAM). However, the computer memory of each of the server and the client devices can be any type of computer memory or any other type of electronic storage medium that is located either internally or externally to the server or the client devices, such as, for example, read-only memory (ROM), compact disc read-only memory (CDROM), electro-optical memory, magneto-optical memory, an erasable programmable read-only memory (EPROM), an electrically-erasable programmable read-only memory (EEPROM), a computer-readable medium, or the like. According to exemplary embodiments, the respective RAM can contain, for example, the operating program for either the server or the respective client device. As will be appreciated based on the following description, the RAM can, for example, be programmed using conventional techniques known to those having ordinary skill in the art of computer programming. The actual source code or object code for carrying out the steps of, for example, a computer program can be stored in the RAM. Each of the server and the client devices can also include a database. The database can be any type of computer database for storing, maintaining, and allowing access to electronic information stored therein. The server preferably resides on a network, such as a local area network (LAN), a wide area network (WAN), a virtual private network (VPN), or the Internet. Each of the client devices preferably is wirelessly connected to the network on which the host server resides, thus enabling electronic communications between the server and the respective client device.

In a preferred embodiment, the directory 105 includes the following components:
  a back-end database whose keys are telephone numbers and whose values are identifiers of applications, for example, e-mail addresses, running on a general purpose computer
  a first network interface that receives queries and sends responses to those queries after consulting the database
  a second network interface that receives provisioning from middleware toolkits to populate the database
  a set of policies for the formulation of responses, based on the preference of users, which are either defaults built into the system or are provisioned directly by the user through a third network interface In a preferred embodiment, the middleware toolkit 110 includes the following components:
  a first network interface for sending provisioning requests to the directory
  a second network interface for sending queries to the directory and receiving responses
  a first application programming interface (API) for receiving provisioning requests from applications
  a second application programming interface for receiving requests for the identifiers associated with a telephone number, and sending responses back to the application The system 100 may be implemented by installing the middleware 110 in a mobile telephone device, where one or more applications 115, such as, for example, a contact book, invoke the middleware toolkit 110. The middleware toolkit 110 communicates over the Internet with the directory 105, either by provisioning the directory 105, or querying for information that has already been provisioned in the directory 105, or both. The application 115 then makes use of the contact information learned by the middleware toolkit 110; the manner in which this information is used by the application 115 varies based on the application's needs. For example, a contact book application could render to the user the various contact addresses associated with applications that it learned from the middleware toolkit 110. The user might then select one of these contact addresses in order to initiate a communication with that application, for example, e-mail.

Figure 3:
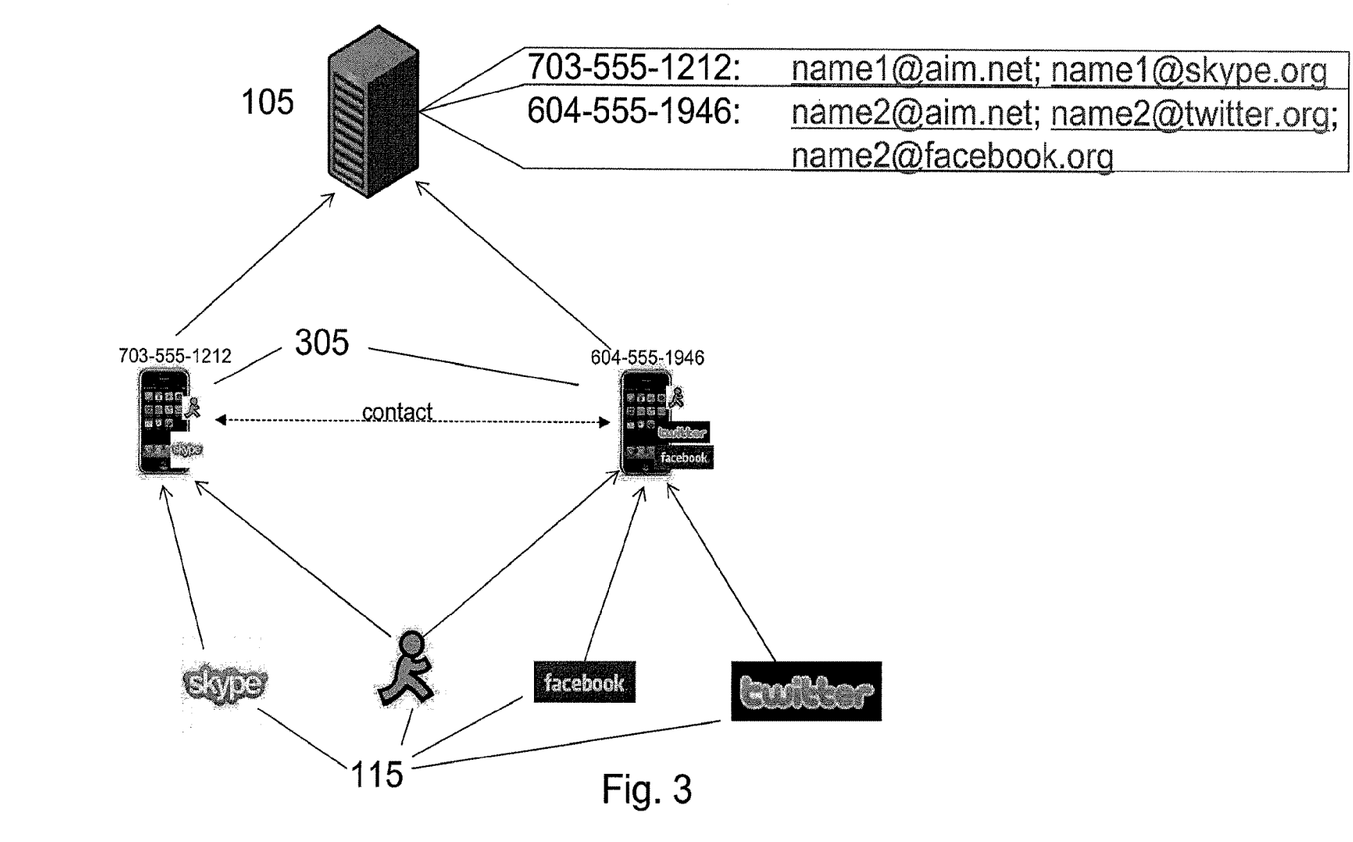
FIG. 3 illustrates a directory containing installed applications and a database for storing provisioned contacting information as used in the system of FIG. 1.

Referring to FIG. 3, in a preferred embodiment of the invention, mobile Internet-enabled smart telephones 305 are typically used by clients of the system 100. The telephones 305 are understood to be general purpose end user devices which have been assigned telephone numbers; for example, the Apple iPhone. The middleware toolkit 110 is incorporated into one or more applications 115 running on the mobile telephone 305, and each of these applications could register an associated communications address with the directory 105.

Figure 4:
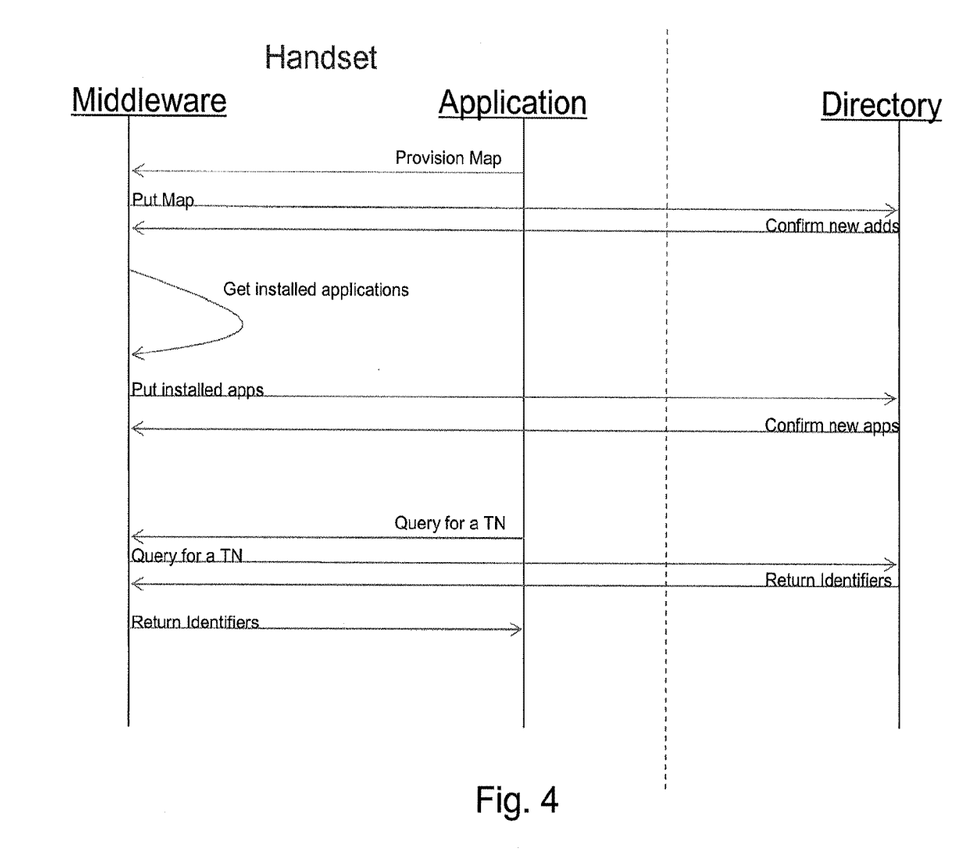
FIG. 4 illustrates an information flow diagram for the provisioning and querying steps of a method for sharing contacting information across applications according to a preferred embodiment of the invention.

Referring to FIG. 4, in a preferred embodiment of the present invention, the directory 105 receives queries and sends responses using a protocol such as ENUM, which is a DNS-based protocol for the mapping of telephone numbers into Uniform Resource Indicators (URIs), which are the identifiers that designate Internet applications such as web pages and e-mail inboxes. The middleware toolbox 110 therefore acts as an ENUM resolver, a type of DNS resolver with additional capabilities to understand NAPTR DNS Resource Records, which contain URIs, and is capable of properly formulating ENUM queries and understanding ENUM replies. The directory 105 is capable of mapping ENUM queries to the keys of its database, extracting the values associated with those keys, and formulating them into NAPTR DNS RR format to be sent back to the client.

One exemplary application 115 that could make use of the URIs returned by the directory 105 is an extension to the iPhone contact book. A user might provision, through the user interface of the iPhone, certain identifiers associated with his own telephone number. The contact book application uploads these identifiers to the directory, along with the list of contacts and associated telephone numbers that the user has provisioned in his contact book. Whenever any of those contacts queries the directory 105 for the user's telephone number, the directory 105 will return the set of provisioned identifiers, which will in turn populate the querying user's entry for the provisioning user in his own contact book. This allows identifiers to spread automatically and seamlessly between contacts, without revealing that information to anyone who is not a contact.

In an alternative embodiment, the system 100 may be implemented by devices that are not tied to mobile telephones, but are identified by telephone numbers. This could include, for example, telephony applications operating on a desktop computer. This could also include applications that run on a general purpose computer operated by a user who also subscribes to a traditional, non-Internet based telephone service, and wishes simply to use that telephone number as a means of identifying various Internet services.

Some external applications might benefit from querying the database to learn which telephone numbers are associated with various applications. For example, a "lobby service" that helps users find partners for online games might query the database externally to learn which games two users have in common as part of a rendezvous activity.

The use of reciprocal authorization works according to the following rule: If a first user has provisioned a second user as a contact, then the second user is authorized to see the identifiers provisioned by the first user, and conversely if the second user has provisioned the first user as a contact, then the first user is authorized to see the identifiers provisioned by the second user. Reciprocal authorization is a simple policy. However, users may desire finer grained policy controls that could, for example, allow particular identifiers to be authorized or forbidden to particular requestors on a case-by-case basis. In a preferred embodiment of the invention, the system may use any acceptable form of authorization, including fine-grained policy controls that make authorization determinations on a case-by-case basis.

While the present invention has been described with respect to what is presently considered to be the preferred embodiment, it is to be understood that the invention is not limited to the disclosed embodiments. To the contrary, the invention is intended to cover various modifications and equivalent arrangements included within the spirit and scope of the appended claims. The scope of the following claims is to be accorded the broadest interpretation so as to encompass all such modifications and equivalent structures and functions.

What is claimed is:

1. A method for mobile application authorization, the method being implemented by one or more processors of a server and comprising:
   receiving, over a network from a first mobile device of a first user, data corresponding to (i) a first phone number of the first mobile device, (ii) a set of account identifiers for the first user, and (iii) a set of phone numbers authorized to access the set of account identifiers;
   receiving, over the network from a second mobile device of a second user, a query including the first phone number of the first mobile device and a second phone number of the second mobile device; and
   in response to determining that the second phone number is in the set of phone numbers authorized to access the set of account identifiers, transmitting, without receiving an authorization signal from the first user in response to the query, one or more account identifiers from the set of account identifiers to the second mobile device.

2. The method of claim 1, further comprising:
   storing, in a server memory of the server, a mapping of the first phone number to the set of account identifiers for the first user and the set of phone numbers authorized to access the set of account identifiers.

3. The method of claim 2, wherein the phone numbers authorized to access the set of account identifiers are access keys to the set of account identifiers in the server memory.

4. The method of claim 1, wherein the second mobile device includes a middleware application that comprises:
   a first application programming interface (API) for receiving requests for account identifiers from applications and transferring responses to the requests to the applications; and
   a second API for transmitting the requests for account identifiers to the server over the network and receiving the responses to the requests from the server.

5. The method of claim 1, wherein the set of account identifiers for the first user includes at least one Uniform Resource Indicator (URI).

6. The method of claim 5, wherein the at least one URI is associated with an identifier selected from the group consisting of an e-mail address, an instant messaging handle, and a Uniform Resource Locator (URL) of a web page.

7. The method of claim 1, wherein transmitting the one or more account identifiers from the set of account identifiers comprises transmitting an SMS text message to the second mobile device.

8. A network server comprising:
   one or more processors; and
   one or more memory resources that access the instructions to:
      receive, over a network from a first mobile device of a first user, data corresponding to (i) a first phone number of the first mobile device, (ii) a set of account identifiers for the first user, and (iii) a set of phone numbers authorized to access the set of account identifiers;
      receive, over the network from a second mobile device of a second user, a query including the first phone number of the first mobile device and a second phone number of the second mobile device; and in response to a determination that the second phone number is in the set of phone numbers authorized to access the set of account identifiers, transmit, without receiving an authorization signal from the first user in response to the query, one or more account identifiers from the set of account identifiers to the second mobile device.

9. The network server of claim 8, wherein the one or more processors access the instructions to:
store, in a server memory of the network server, a mapping of the first phone number to the set of account identifiers for the first user and the set of phone numbers authorized to access the set of account identifiers.

10. The network server of claim 9, wherein the phone numbers authorized to access the set of account identifiers are access keys to the set of account identifiers in the server memory.

11. The network server of claim 8, wherein the second mobile device includes a middleware application that comprises:
a first application programming interface (API) for receiving requests for account identifiers from applications and transferring responses to the requests to the applications; and
a second API for transmitting the requests for account identifiers to the network server over the network and receiving the responses to the requests from the network server.

12. The network server of claim 8, wherein the set of account identifiers for the first user includes at least one Uniform Resource Indicator (URI).

13. The network server of claim 12, wherein the at least one URI is associated with an identifier selected from the group consisting of an e-mail address, an instant messaging handle, and a Uniform Resource Locator (URL) of a web page.

14. The network server of claim 8, wherein transmitting the one or more account identifiers from the set of account identifiers comprises transmitting an SMS text message to the second mobile device.

15. A non-transitory computer-readable medium that stores instructions, executable by one or more processors of a network server, to cause the network server to perform operations that comprise:
receiving, over a network from a first mobile device of a first user, data corresponding to (i) a first phone number of the first mobile device, (ii) a set of account identifiers for the first user, and (iii) a set of phone numbers authorized to access the set of account identifiers;
receiving, over the network from a second mobile device of a second user, a query including the first phone number of the first mobile device and a second phone number of the second mobile device; and
in response to determining that the second phone number is in the set of phone numbers authorized to access the set of account identifiers, transmitting, without receiving an authorization signal from the first user in response to the query, one or more account identifiers from the set of account identifiers to the second mobile device.

16. The non-transitory computer-readable medium of claim 15, wherein the instructions, when executed by the one or more processors, cause the network server to perform operations that comprise:
storing, in a server memory of the network server, a mapping of the first phone number to the set of account identifiers for the first user and the set of phone numbers authorized to access the set of account identifiers.

17. The non-transitory computer-readable medium of claim 16, wherein the phone numbers authorized to access the set of account identifiers are access keys to the set of account identifiers in the server memory.

18. The non-transitory computer-readable medium of claim 15, wherein the second mobile device includes a middleware application that comprises:
a first application programming interface (API) for receiving requests for account identifiers from applications and transferring responses to the requests to the applications; and
a second API for transmitting the requests for account identifiers to the network server over the network and receiving the responses to the requests from the network server.

19. The non-transitory computer-readable medium of claim 15, wherein the set of account identifiers for the first user includes at least one Uniform Resource Indicator (URI).

20. The non-transitory computer-readable medium of claim 19, wherein the at least one URI is associated with an identifier selected from the group consisting of an e-mail address, an instant messaging handle, and a Uniform Resource Locator (URL) of a web page.

* * * * *